United States Patent
Rodriguez et al.

[11] Patent Number: 5,484,401
[45] Date of Patent: Jan. 16, 1996

[54] TREATMENT METHOD FOR PLEURAL EFFUSION

[75] Inventors: Michael Rodriguez, Nashville, Tenn.; Bonnie B. Vivian, Evergreen; Shirley K. Freeman, Pine, both of Colo.

[73] Assignee: Denver Biomaterials, Inc., Evergreen, Colo.

[21] Appl. No.: 251,692

[22] Filed: May 31, 1994

Related U.S. Application Data

[63] Continuation-in-part of Ser. No. 971,722, Nov. 4, 1992, abandoned.

[51] Int. Cl.[6] .......................... A61M 39/04; A61M 39/24
[52] U.S. Cl. ................................ 604/28; 604/49
[58] Field of Search ...................... 604/175, 280, 604/49, 28, 167, 256

[56] References Cited

U.S. PATENT DOCUMENTS

| | | | |
|---|---|---|---|
| 4,669,463 | 6/1987 | McConnell | 604/256 |
| 4,874,377 | 10/1989 | Newgard et al. | 604/256 |
| 4,929,235 | 5/1990 | Merry et al. | 604/256 |
| 4,944,732 | 7/1990 | Russo | 604/256 |
| 4,946,449 | 8/1990 | Davis, Jr. | 604/256 |
| 4,960,412 | 10/1990 | Fink | 604/256 |
| 4,973,311 | 11/1990 | Iwakoski et al. | 604/35 |
| 5,009,636 | 4/1991 | Wortley et al. | 604/280 |
| 5,057,084 | 10/1991 | Ensminger et al. | 604/256 |
| 5,061,255 | 10/1991 | Greenfield et al. | 604/35 |
| 5,064,416 | 11/1991 | Newgard et al. | 604/256 |
| 5,098,405 | 3/1992 | Peterson et al. | 604/256 |
| 5,106,054 | 4/1992 | Mollenauer et al. | |
| 5,141,499 | 8/1992 | Zappacosta | 604/280 |
| 5,156,597 | 10/1992 | Verrett et al. | |
| 5,207,655 | 5/1993 | Sheridan | 604/280 |

*Primary Examiner*—Paul J. Hirsch
*Attorney, Agent, or Firm*—Beaton & Folsom

[57] ABSTRACT

A method for treating a pleural effusion condition by establishing fluid communication with a pleural space, using a catheter attached to a valve that is normally closed but openable by the insertion of a tube in the side opposite the catheter. The catheter is implanted into the pleural space and is periodically accessed by inserting a tube into the valve on the side opposite the catheter to add or remove fluid to and from the pleural space using a negative pressure source.

2 Claims, 3 Drawing Sheets

TREATMENT METHOD FOR PLEURAL EFFUSION

This application is a continuation-in-part of application Ser. No. 07/971,722 filed Nov. 4, 1992 abandoned.

FIELD OF THE INVENTION

The present invention relates to the field of removing pleural effusion fluids and, in particular, to a therapeutic treatment method for removing pleural effusion fluid using long-term catheter implantation into the pleural space.

BACKGROUND OF THE INVENTION

Pleural effusion refers to the effusion of fluid into the pleural space. The pleural space normally contains approximately 5 to 20 ml of fluid. The pH, glucose and electrolytes of the fluid are equilibrated with plasma, but the fluid is relatively protein-free. The fluid is the result of the hydrostatic-oncotic pressure of the capillaries of the parietal pleura. About 80–90% of the fluid is reabsorbed by the pulmonary venous capillaries of the visceral pleura, and the remaining 10–20% is reabsorbed by the pleural lymphatic system. The turnover of fluid in the pleural space is normally quite rapid—roughly 35 to 75% per hour, so that 5 to 10 liters of fluid move through the pleural space each day.

A disruption in the balance between the movement of fluid into the pleural space and the movement of fluid out of the pleural space may produce excessive fluid accumulation in the pleural space. Such disruptions may include, for example, (1) increased capillary permeability resulting from inflammatory processes such as pneumonia, (2) increased hydrostatic pressure as in congestive heart failure, (3) increased negative intrapleural pressure as seen in atelectasis, (4) decreased oncotic pressure as occurs in the nephrotic syndrome with hypoalbuminemia, and (5) increased oncotic pressure of pleural fluid as occurs in the inflammation of pleural tumor growth or infection. Pleural effusion is particularly common in patients with disseminated breast cancer, lung cancer or lymphatic cancer and patients with congestive heart failure, but also occurs in patients with nearly all other forms of malignancy.

The clinical manifestations of pleural effusion include dyspnea, cough and chest pain which diminish the patient's quality of life. Although pleural effusion typically occurs toward the end of terminal malignancies such as breast cancer, it occurs earlier in other diseases. Therefore relieving the clinical manifestations of pleural effusion is of a real and extended advantage to the patient. For example, non-breast cancer patients with pleural effusion have been known to survive for years. See "Pleural Effusion in Cancer Patients", Izbicki, et al., *Cancer* October 1975, p. 1511.

There are a number of treatments for pleural effusion. If the patient is asymptomatic and the effusion is known to be malignant or paramalignant, treatment may not be required. Such patients may develop progressive pleural effusions that eventually do produce symptoms requiring treatment, but some will reach a stage where the effusions and reabsorption reach an equilibrium that is still asymptomatic and does not necessitate treatment.

Pleurectomy and pleural abrasion is generally effective in obliterating the pleural space and, thus, controlling the malignant pleural effusion. This procedure is done in many patients who undergo thoracotomy for an undiagnosed pleural effusion and are found to have malignancy, since this would prevent the subsequent development of a symptomatic pleural effusion. However, pleurectomy is a major surgical procedure associated with substantial morbidity and some mortality. Therefore, this procedure is usually reserved for patients with an expected survival of at least several months, who are in relative good condition, who have a trapped lung, or who have failed a sclerosing agent procedure.

In general, systemic chemotherapy is disappointing for the control of malignant pleural effusions. However, patients with lymphoma, breast cancer, or small cell carcinoma of the lung may obtain an excellent response to chemotherapy.

Another approach to removing fluid from the pleural space is to surgically implant a chest tube. Such tubes are commonly quite rigid and fairly large in diameter and are implanted by making a surgical incision and spreading apart adjacent ribs to fit the tube into place. Such procedures are painful to the patient, both initially when the chest tube is inserted and during the time it remains within the pleural space.

Thoracentesis is a common approach to removing pleural fluid, in which a needled catheter is introduced into the pleural space through an incision in the chest cavity and fluid is positively drawn out through the catheter using a syringe or a vacuum source. The procedure may also include aspiration utilizing a separate syringe. There are a number of difficulties in thoracentesis, including the risk of puncturing a lung with the catheter tip or with the needle used to introduce the catheter, the risk of collapsing a lung by relieving the negative pressure in the pleural space, the possibility of aggravating the pleural effusion by stimulating fluid production in the introduction of the catheter, and the risk of infection. One of the primary difficulties with ordinary thoracentesis procedures is that fluid reaccumulates in the pleural space relatively quickly after the procedure is performed, and so it is necessary to perform the procedure repeatedly—as often as every few days. In fact, some studies found that the fluid re-accumulates in one to three days in most cases and re-accumulates within a month in 97% of the cases studied. See "Diagnosis and Treatment of Malignant Pleural Effusion", F. J. Hausheer, J. W. Yarbro, *Seminars in Oncology*, March 1985, p. 54; "Malignant Effusion", Anderson, et al., *Cancer*, April 1974, p. 916. Of course, each time the procedure is repeated the risks identified above are heightened. Moreover, the comfort to the patient resulting from the procedure begins to be offset by the discomfort of the procedure itself.

There is therefore a need for a treatment method for removing pleural effusion which does not require repeated invasion of the pleural space in a manner which produces repeated patient discomfort, infection risks, risks of accidental trauma to the lungs, and the potential for stimulating fluid production. Ideally, such a method and apparatus would employ instruments that are relatively simple in design and manufacture and would be within the capabilities of ordinary physicians to use, and would involve at least the possibility of reducing future pleural effusion.

SUMMARY OF THE INVENTION

The present invention is a method for draining pleural effusion fluids using a special catheter device that is implanted in the pleural space for extended periods of time. The proximal end of the catheter is fenestrated to receive the pleural fluid and the distal end is in communication with a vacuum source or negative pressure source to draw fluid from the pleural space into the catheter through the multiple orifices, and through the catheter toward the negative pressure source.

Between the negative pressure source and the distal end of the catheter is a valve to close the catheter when the negative pressure source is not connected to the catheter between fluid removals, and to open the catheter when the negative pressure source is connected to the catheter for the removal of fluid. The valve is normally closed, so that fluid does not drain through the catheter and air does not enter the catheter when the negative pressure source is not connected to the catheter, but opens when the apparatus is configured for fluid removal, as upon connection of the negative pressure source. The valve is also designed such that a tube can be introduced into the valve to apply fluids therein, thereby allowing the introduction of materials into the pleural space if desired. The valve may be capped by a cap which may include an antimicrobial and/or antibacterial solution to avoid contamination.

The treatment method is straight-forward and highly effective in that accumulated pleural effusion fluid can be drained whenever desired without re-entering the pleural space. The design of the implanted instrument is such that the chance of infection or contamination is minimized. Moreover, unlike other draining procedures such as periodic thoracentesis, it is believed that the frequent draining of the pleural space may produce a sclerosis that will prevent or lessen further effusion, thereby alleviating the condition altogether.

DETAILED DESCRIPTION OF THE INVENTION

Figure 1:
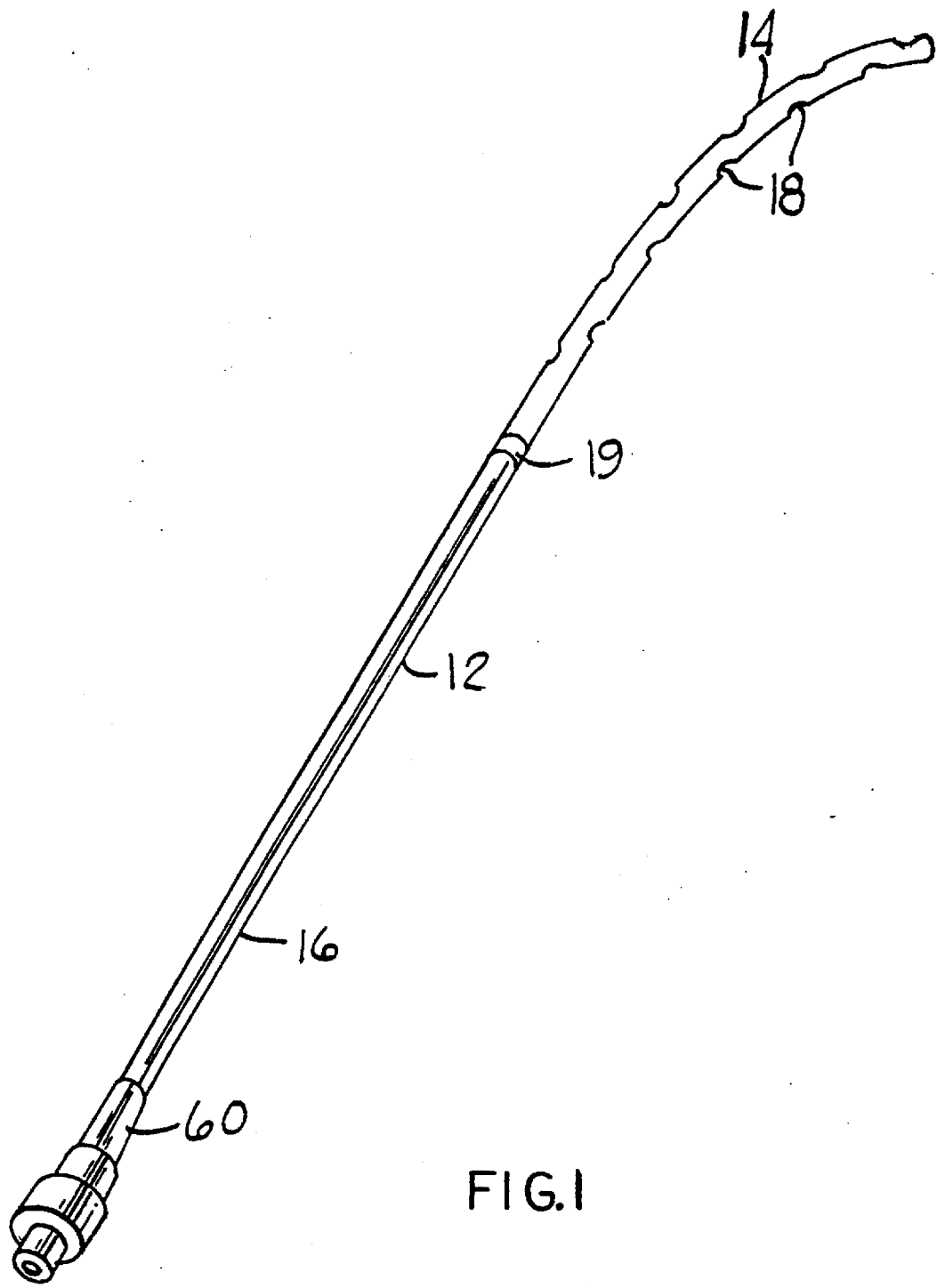
FIG. 1 is a pictorial view of the catheter of the present invention prepared for implantation.

A pictorial view of a catheter 12 for use with the present invention is shown in FIG. 1. The catheter 12 in a preferred embodiment has a proximal end 14 and a distal end 16 may be about twenty-four inches long, the proximal ten inches being fenestrated with a series of holes 18 allowing fluid communication between the exterior of the catheter and the lumen. The catheter is made of a flexible material such as silicone rubber. A few inches distal from the holes 18 may be a Dacron cuff 19.

The catheter is implanted into the pleural space using procedures known in the art. For example, one technique is to make an incision between adjacent ribs of the patient's rib cage in a direction superiorly and posteriorly toward the pleural space. The pleural space is aspirated using a needle and then a J-wire is inserted through the needle and into the pleural space and the needle is removed. A sheath and dilator are threaded over the J-wire and into the pleural space and the J-wire is removed. The dilator is removed from within the sheath. The catheter is then threaded through the sheath and into the pleural space and the sheath is removed.

Figure 2:
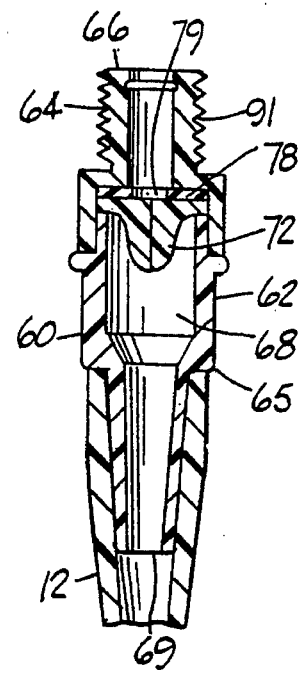
FIG. 2 is a partially sectional view of the valve utilized in an embodiment of the invention.

The distal end 16 of the catheter 12 is attached to a valve 60. The valve 60 is shown in detail in FIG. 2. As shown in FIG. 2, the valve includes a body 62 having a distal portion 64 and a proximal portion 65 which are attached to one another by an adhesive or other suitable means. The end 66 of the distal portion 64 and the end 69 of the proximal portion 65 each have a hole, and the centers of those portions 64 and 65 are hollowed out, thereby forming a passageway 68 through the valve body 62. Positioned within this passageway 68 is a "duckbill" valve 72 which is of the type known in the art consisting of an elastomeric, molded, one-piece dome containing a slit in the center of the domed portion. The duckbill valve 72 may be opened by inserting an elongated member through the passageway 68 from the distal portion 64 to pry apart the valve in the manner described below. Adjacent to the duckbill valve 72 toward the distal portion 64 is an elastomeric seal 78. The elastomeric seal 78 is a disk-shaped element having a hole 79 through the center to seal against the outside of the drainage tube 110 or introduction tube 150 in the manner described below.

Figure 3:
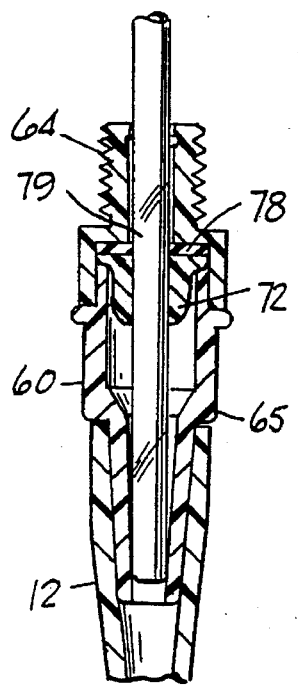
FIG. 3 is a partially sectional view of the valve of FIG. 2, with a tube inserted therein to open the valve.
Figure 4:
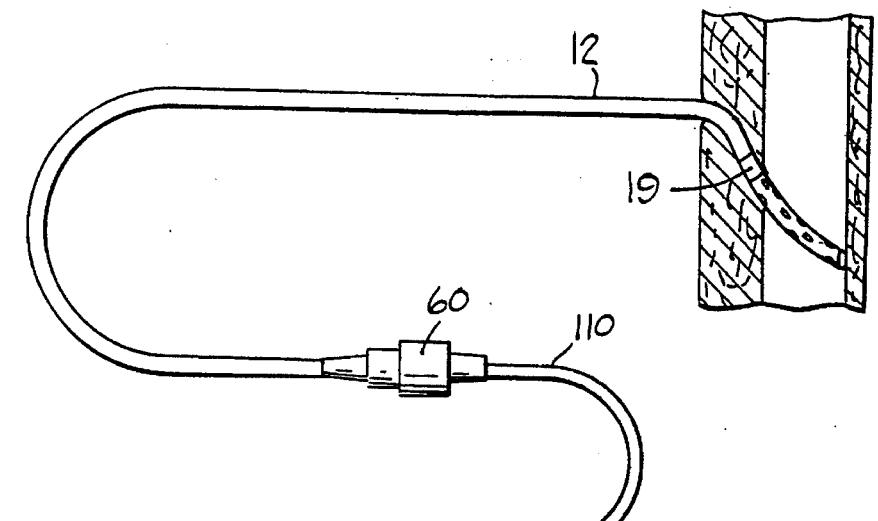
FIG. 4 is a diagrammatic view of the apparatus of the present invention including a vacuum bottle to produce a negative pressure on the proximal end of the catheter.
Figure 4:
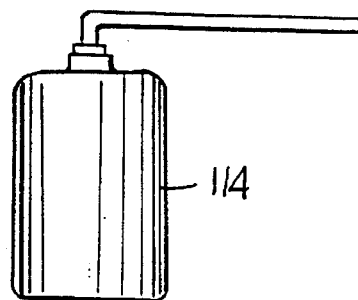

Fluid is withdrawn from the pleural space by inserting a drainage tube 110 into the distal portion 64 of the valve 60 as shown in FIGS. 3–4. The drainage tube is slightly larger in its outside diameter then the hole 79 in the elastomeric seal 78, thereby ensuring that a seal is created between the elastomeric seal 78 and the outside of the drainage tube to prevent fluid from leaking. The insertion of the drainage tube 110 into the valve 60 opens the duckbill valve 72 and thereby accesses the interior of the catheter 12. As shown in FIG. 4, the other end of the drainage tube 110 may be in communication with a vacuum bottle 114 or any other negative pressure source such as a mechanical device to draw fluid from the pleural space, into the catheter, through the catheter and the valve, through the drainage tube and into a fluid collection reservoir or the vacuum bottle.

The fluid removal procedure is discontinued by simply withdrawing the drainage tube 110 from the valve 60. As the end of the drainage tube comes out of the duckbill valve 72, the valve closes and prevents further fluid from flowing out of the valve and also prevents air from entering the catheter and possibly flowing into the pleural space.

Figure 5:
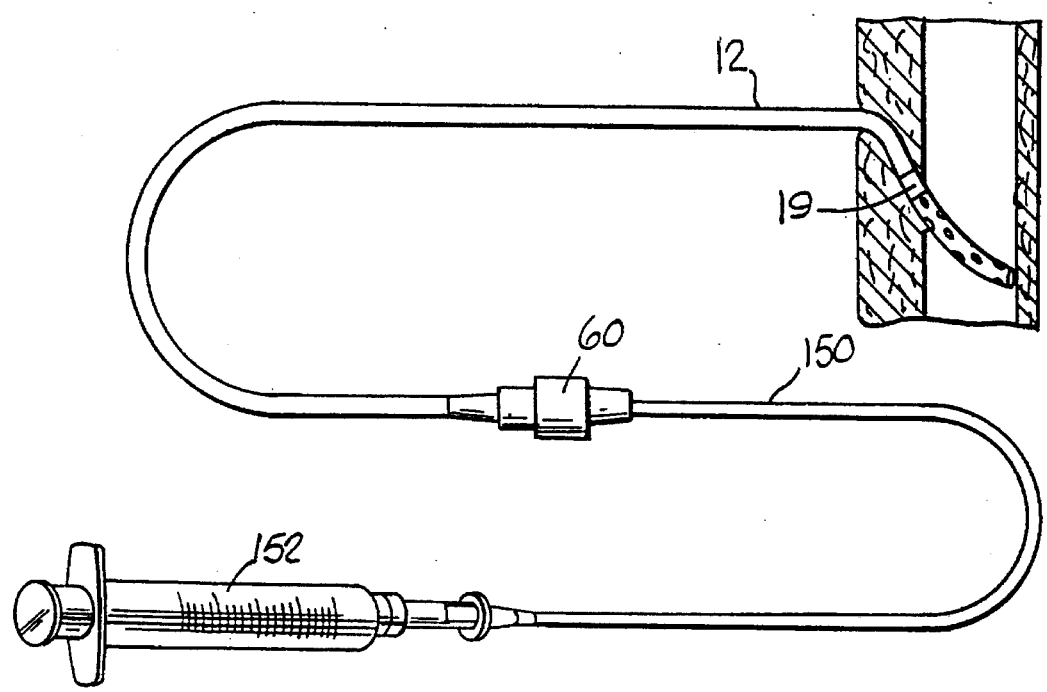
FIG. 5 is a diagrammatic view of the apparatus of the present invention including a syringe to introduce fluid into the catheter.

A similar procedure can be used to introduce material into the pleural space as shown in FIG. 5, using the same implanted catheter 12 and attached valve 60. Rather than utilizing a drainage tube 110, an introduction tube 150 of the same configuration is used. One end of the introduction tube is attached to a syringe 152 (or infusion pump or other known device for introducing fluid into the body) and the other end is inserted into the valve 60. The end of the introduction tube 150, like the end of the drainage tube 110 previously described, goes through and seals against the hole 79 of the elastomeric seal 78, and then opens and goes through the duckbill valve 72 to access the catheter lumen. Thus, leak-proof communication is established from the syringe interior to the pleural space.

Figure 6:
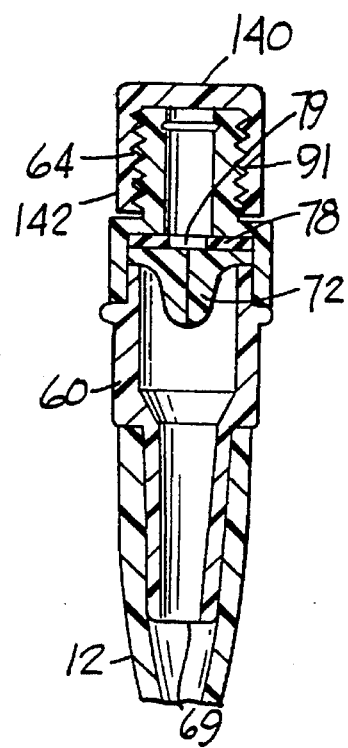
FIG. 6 is a partially sectional view of the valve utilized in an embodiment of the invention with a valve cap.

The distal end 64 of the valve 60 may be capped with a cap 140 as shown in FIG. 6 when fluid is not being removed from or introduced to the pleural space. The cap 140 is not necessary to close the valve, since the valve is already closed by the duckbill valve 72 in the passageway 68 when there is no drainage tube or introduction tube. However, it may still be desirable to cap the valve to prevent contamination of the passageway 68 and to reduce the possibility of infection. The cap 140 may have a threaded sleeve 142 to mate with threads on the valve 60. To further reduce the possibility of infection, the cap 140 may be of the sterilant-filled type in which the cap is stored in a chamber with mating threads which is filled with a sterilant such as iodine when the cap is not in use.

The present treatment method is superior to palliative treatments known in the art in several important respects. The present treatment method requires only a single invasion of the pleural space, as contrasted with multiple invasion procedures such as periodic thoracentesis. The indwelling catheter is readily available at any time for drainage of pleural effusion fluid as required. Also, the catheter can be used to introduce substances such as a sclerosing agent if desired. Even though the treatment involves an indwelling catheter, the special design of the instruments as described minimize the likelihood of infection or contamination which would ordinarily be expected for an in-dwelling catheter. Perhaps most importantly, it is believed that, at least for some patients, the method is not merely palliative but is remedial as well due to a sclerosing effect in the pleural space produced by the dryness resulting from frequent draining.

We claim:

1. Method of producing a sclerosing effect in the pleural of a human to reduce pleural effusion, comprising inserting a catheter through the chest wall of the patient so that an end of the catheter is in the pleural space; repeatedly accessing the pleural space to repeatedly drain pleural effusion from the pleural space by inserting a tube into a valve in the catheter to open the valve and access the catheter, to produce a sclerosing effect in the pleural space to reduce pleural effusion.

2. The method of claim 1, further comprising introducing a sclerosing agent into the pleural space through the tube and catheter.

* * * * *